United States Patent

Dolbier, Jr. et al.

Patent Number: 6,150,499
Date of Patent: *Nov. 21, 2000

[54] PROCESS FOR PREPARATION OF TFPX-DICHLORIDE

[75] Inventors: William R. Dolbier, Jr.; Jianxin Duan, both of Gainesville, Fla.

[73] Assignee: Specialty Coating Systems, Inc., Jersey City, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/003,208

[22] Filed: Jan. 6, 1998

[51] Int. Cl.$^7$ ..................................................... C08G 61/00
[52] U.S. Cl. ........................... 528/397; 528/392; 528/401; 528/497; 528/499; 528/501; 528/502 R; 528/503
[58] Field of Search ..................................... 528/397, 392, 528/401, 497, 499, 501, 502 R, 503

[56] References Cited

FOREIGN PATENT DOCUMENTS 6118072  4/1994  Japan .
2032654  4/1995  Russian Federation .

OTHER PUBLICATIONS

Milos Hudlicky, "Chemistry of Organic Fluorine Compounds", 2$^{nd}$ Edition, Ellis Horwood Limited, New York, pp. 96, 103, 105, 112–128, 130 and 759, 795 and 763 1976.

Milos Hudlicky and Attila E. Pavlath, "Chemistry of Organic Fluorine Compounds II, A Critical Review".

Milos Monograph 187, American Chemical Society, Washington, D.C., pp. 187–192 and p. 198, 1995.

Occidental Chemical Corporation, Specialty Chemicals, p–Xylene Derivatives.

*Primary Examiner*—Duc Truong
*Attorney, Agent, or Firm*—Mintz, Levin, Cohn, Ferris, Glovsky and Popeo, P.C.

[57] ABSTRACT

A method for the synthesis of TFPX-dichloride is disclosed. The method involves reacting hexachloro-p-xylene with anhydrous HF in an inert organic solvent. The reaction is advantageous in that it produces relatively high yields of TFPX-dichloride, provides little waste, and is carried out as a simple, one-step process.

23 Claims, No Drawings

PROCESS FOR PREPARATION OF TFPX-DICHLORIDE

FIELD OF THE INVENTION

This invention is in the field of chemical synthesis. More particularly, the invention relates to a method for the preparation of 1,4-bis-(chlorodifluoromethyl) benzene (hereafter referred to as "TFPX-Dichloride").

BACKGROUND OF THE INVENTION

Dielectric films are widely used throughout both the electronics and coatings industries. Due to their relatively high dielectric constants and melting points, there is an increasing interest in forming dielectric layers from parylene polymers having the molecular structure:

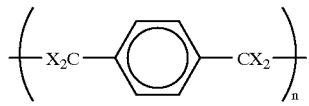

wherein X is typically a hydrogen atom or a fluorine atom.

Parylene polymers are usually formed by chemical vapor deposition processes. One such process is the Gorham process in which a parylene dimer have the molecular structure:

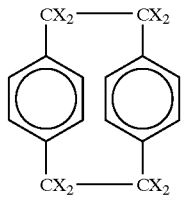

is vaporized and the dimer bonds are then cleaved to yield parylene monomers. The parylene monomers are deposited onto a surface and subsequently polymerized. Because the dielectric constant and melting temperature of parylene polymers usually increases as the number of fluorine atoms within the polymer increases, it is desirable to use octafluoro-[2,2]paracyclophane (hereafter "AF4") having the molecular structure:

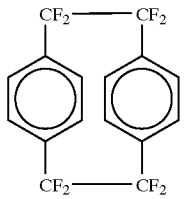

as the parylene dimer.

TFPX-dichloride having the following structure:

is one preferred starting material for the preparation of AF4. Heretofore, the only useful preparation of TFPX-dichloride has been via a high yield, photo-induced chlorination of α,α,α',α'-tetrafluoro-p-xylene, (hereafter "TFPX"), having the following structure:

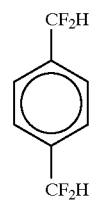

Unfortunately, however, all currently available methods for preparation of TFPX are expensive and/or produce undesirable amounts of hazardous waste. Additionally, known methods for production of TFPX are not readily adapted to industrial-scale processes.

The conventional procedure for synthesizing TFPX involves the fluorination of terephthaldehyde, which has the molecular structure:

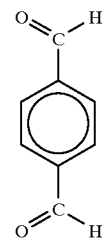

$SF_4$ and $MoF_6$ are the most commonly used reagents for terephthaldehyde fluorination. However, $SF_4$ and $MoF_6$ are expensive, reducing the industrial utility of this synthetic scheme. In addition, $SF_4$ and $MoF_6$ are toxic materials, so a large amount of hazardous waste is produced using these reagents.

Russian Patent No. 2,032,654 discloses an alternate method of synthesizing TFPX in which α,α,α',α'-tetrabromo-p-xylene (hereafter "TBPX") having the molecular structure:

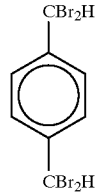

is reacted with $SbF_3$ to produce TFPX. This method employs the well established electrophilic catalyzed $S_N1$ reaction mechanism for replacement of benzylic halogen atoms of the TBPX with fluorine atoms. According to this method, the antimony atom in SbF$_3$ acts as an electrophile which removes bromine from TBPX to form a carbocation. The carbocation subsequently reacts with fluorine to form TFPX. While this reaction is reported to provide a good yield when carried out under comparatively mild reaction conditions, antimony-containing compounds are highly toxic and expensive. Furthermore, the SbF$_3$ is used in a stoichiometric amount rather than a catalytic amount, resulting in large quantities of hazardous waste materials. Therefore, this method of synthesizing TFPX has limited use for industrial applications.

Finally, TFPX has been synthesized by the reaction of nucleophilic fluorine molecules with non-fluorinated tetrahalo-p-xylenes via S$_N$2 type nucleophilic displacement reactions. In such synthesis, the benzylic halogen atoms of a non-fluorinated tetrahalo-p-xylene are replaced by the fluorine atoms in a nucleophilic fluorine molecule without formation of a carbocation intermediate. Examples of such reactions include the reaction of α,α,α',α'-tetrachloro-p-xylene with CsF or KF. This procedure, while being less expensive and producing less hazardous waste has recently been found to be very difficult to achieve on an industrial scale.

Despite the various methods for synthesizing TFPX, which is an excellent precursor of TFPX-dichloride, a need still exists for a simple, environmentally friendly process for making TFPX-dichloride which utilizes inexpensive, readily-available reactants, and which is scaleable to an industrial level of production.

SUMMARY OF THE INVENTION

The present invention relates to the synthesis of TFPX-dichloride, not from TFPX, but from hexachloro-p-xylene, (an inexpensive, readily-available starting material which is prepared by a high-yield, exhaustive chlorination of p-xylene). In this process, the hexachloro-p-xylene is suspended, and partially dissolved, in a minimum amount of an inert solvent and reacted with anhydrous HF. The resulting precursor to AF4 is provided in high yield and high purity via a one step process using readily available and inexpensive reactants. As such, the process provides significant economic advantages over other methods for the preparation of TFPX-dichloride, all of which require the use of TFPX as a precursor.

More particularly, in one preferred embodiment, the present invention relates to a process for the synthesis of TFPX-dichloride in which hexachloro-p-xylene in 1,2-dichloroethane is reacted with anhydrous HF at room temperature to produce high yields of TFPX-dichloride.

DETAILED DESCRIPTION OF THE INVENTION

As noted above, the invention relates to the synthesis of TFPX-dichloride by reacting hexachloro-p-xylene and HF. The reaction is carried out using a relatively small amount of an inert solvent. A preferred solvent is 1,2-dichloroethane. The reaction is of particular interest because high yields of TFPX-dichloride can be provided in a one-step process using readily available and inexpensive starting materials. The reaction is highly specific for forming the desired TFPX-dichloride under mild conditions. The reaction has been observed to progress to a desired level of exchange between chlorine and fluorine constituents and then stop. In addition to the simplicity of the reaction, it is environmentally advantageous because it allows the solvent to be recycled, and it requires only slightly more than the stoichiometric amount of HF. Furthermore, any over-fluorinated byproducts of the reaction are valuable and in demand as reactants in other procedures, and any under-fluorinated byproducts may be recycled. As such, the reaction involves very little waste.

As used herein, the term "hexachloro-p-xylene" (HCPX) denotes a molecule having the structure:

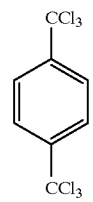

The reaction of hexachloro-p-xylene with HF typically takes place at or near room temperature. If the reaction is carried out in a closed reaction vessel, the pressure has been observed to increase somewhat over the course of the reaction. The increase in pressure is caused by residual gaseous HF as well as gaseous HCl formed during the reaction. Prior to removing the desired TFPX-dichloride product, these gasses may be vented into aqueous NaOH or other suitable medium to cause them to be neutralized.

Although not intending to be limited by specific reaction temperatures, the reaction must be carried out at a temperature sufficiently high to allow the reaction to proceed at a reasonable rate. However, if the reaction temperature is too high, undesirable side reactions, including over-fluorination and polymerization or elimination reactions that form tarry materials, may also occur. Thus, the reaction mixture is ideally maintained at a temperature high enough to form TFPX-dichloride without resulting in undesirable side reactions.

A number of other solvents can be used as the non-interactive organic solvent in the process. These include methylene chloride; 1,1,2,2-tetrachloroethane, pentane, hexane, toluene, trifluorotoluene, and hexafluoro-p-xylene. For the most part, these solvents have proven to be equally efficacious in causing the selective reaction to occur. This suggests that virtually any solvent which dissolves hexachloro-p-xylene and TFPX-dichloride, yet which is not miscible or reactive with HF may be used. Thus, in addition to the previous considerations, the solvent may be chosen simply on the basis of the solvent's boiling point (i.e., it should be easily separable from the products), its cost and environmental considerations.

Electrophilic catalysis, including but not limited to SbCl$_3$, SbCl$_5$, SbF$_3$, SbF$_5$, HgF$_2$ and SnCl$_4$, may also be used in amounts of 1–10% of the moles of hexachloro-p-xylene which is to be fluorinated. The use of such catalysts allows the use of a lower temperature and reduced time of reaction, but they also lead to the production of greater amounts of over-fluorinated products.

Variable times, ranging from 10 hours to 48 hours have been used for the reaction, and temperatures ranging from 10° C. to 30° C. have been used without significant modification of the results.

Thus, the use of hexachloro-p-xylene with a HF in a wide variety of inert organic solvents provides high yields of desired TFPX-dichloride product under relatively mild reaction conditions.

The following examples are intended to be illustrative only and should not be construed as limiting.

EXAMPLE 1

350 g (1.1 mol) of hexachloro-p-xylene (HCPX) was placed into a 600 ml autoclave. 100 ml of 1,2-dichloroethane (DCE) and 200 g (10 mol) anhydrous HF were added. The mixture was stirred at room temperature for about 10 hours, during which time the pressure rose to approximately 3 atmospheres. Upon completion of the reaction, residual HF and HCl were removed by venting into 300 ml of 10% NaOH. The residual organic phase was then washed three times with 100 ml of 5% NaOH and then three times with 300 ml water. Subsequently, the organic phase was dried over MgSO4. Simple distillation gave three fractions:

Fraction 1 (71–90° C.) yielded 27.5 g of material comprising approximately 68% TFPX-dichloride. Of the remaining material, a major portion comprised a pentafluorochloro product.

Fraction 2 (90–95° C.) yielded 174 g of product comprising approximately 97% TFPX-dichloride.

Fraction 3 (95–107° C.) yielded 37 g product comprising approximately 69% TFPX-dichloride. Among the remaining 31% by-product, the major component was trifluorotrychloro material.

Since the theoretical yield of TFPX-dichloride is 1.1 moles of product having a molecular weight of 246.9 g/mol (therefore 271.6 g), and since the reaction provided 213 g of TFPX-dichloride product, the total yield of TFPX-dichloride from the above reaction was about 78.4%.

EXAMPLE 2

2 kg (6.3 mol) of HCPX was placed in a one gallon autoclave. 600 ml of DCE and 540 g (28.4 mol) anhydrous HF were added. The mixture was stirred at autogenous pressure at 30° C. for 20 hours, after which residual HF and HCl were removed by venting into 2 liters of 10% NaOH. The residual organic phase was then washed three times each with 5% NaOH and water, dried over $MgSO_4$, and distilled (boiling point of product, 90–95° C.) to yield 933 g (60% yield) of TFPX-dichloride product. Most of the side product was in the distillation residue which consisted largely of under-fluorinated products. These under-fluorinated products could be recycled and used in subsequent runs.

EXAMPLE 3

350 g (1.1 mol) hexachloro-p-xylene (HCPX), and 100 ml methylene chloride ($CH_2Cl_2$) were placed in a 600 ml autoclave. The mixture was stirred at about 20° C. for 48 hours, at which time the same isolation workup as in Example 1 was carried out. The resulting product yielded 52% TFPX-dichloride along with 2% TFPX-monochloride, 10% TFPX-trichloride, and 28% TFPX-tetrachloride. The trichloride and tetrachloride products are desirable in that they may be recycled and used in subsequent runs.

EQUIVALENTS

From the foregoing detailed description of the specific embodiments of the invention, it should be apparent that a unique reaction for the formation of TFPX-dichloride has been described. Although particular embodiments have been disclosed herein in detail, this has been done for purposes of illustration only, and is not intended to be limiting with respect to the scope of the appended claims which follow. In particular, it is contemplated by the inventors that various substitutions, alterations, and modifications may be made to the invention without departing from the spirit and scope of the invention as defined by the claims. For instance, the choice of a particular inert organic solvent or of particular reaction temperatures is believed to be a matter of routine for a person of ordinary skill in the art with knowledge of the embodiments described herein.

We claim:
1. A synthesis method comprising the steps of:
    a) providing a first reactant comprising hexachloro-p-xylene;
    b) providing a second reactant comprising anhydrous HF;
    c) providing an organic solvent, the solvent being substantially immiscible with HF and substantially nonreactive with HF and hexachloro-p-xylene; and
    d) reacting the first and second reactants in the organic solvent to form a product comprising TFPX-dichloride.
2. The method of claim 1 wherein the organic solvent is selected from the group consisting of methylene chloride, 1,1,2,2-tetrachloroethane, pentane, hexane, toluene, 1,2-dichloroethane and mixtures thereof.
3. The method of claim 1 wherein the organic solvent comprises 1,2-dichloroethane.
4. The method of claim 1 wherein the reaction is carried out at a temperature in the range of approximately 10° C. to approximately 30° C.
5. The method of claim 1 wherein the reaction is allowed to continue from about 10 hours to about 48 hours.
6. The method of claim 5 wherein the reaction is allowed to continue from about 10 hours to about 48 hours.
7. The method of claim 1 which includes the additional step of isolating TFPX-dichloride from the product.
8. The method of claim 7 wherein the isolation comprises distillation.
9. The method of claim 7 which includes the additional step of washing and drying the product prior to the isolation step.
10. The method of claim 9 wherein the washing involves rinsing the product with aqueous NaOH and then rinsing the product with water.
11. The method of claim 7 which includes the additional step of reacting the TFPX-dichloride product to form a parylene dimer comprising octafluoro-[2,2]paracyclophane.
12. The method of claim 11 which includes the additional step of reacting the parylene dimer using the Gorham process to form polymeric parylene.
13. The method of claim 1 wherein the reaction is carried out in the presence of a catalyst.
14. The method of claim 13 wherein the catalyst is selected from the group consisting of $SbCl_3$, $SbCl_5$, $SbF_3$, $SbF_5$, $HgF_2$ and $SnCl_4$.
15. The method of claim 14 wherein the catalyst is present in amounts of 1–10% of the moles of hexachloro-p-xylene.
16. A synthesis method comprising the steps of:
    a) providing a first reactant comprising hexachloro-p-xylene;
    b) providing a second reactant comprising anhydrous HF;
    c) providing an organic solvent comprising 1,2-dichloroethane; and
    d) reacting the first and second reactants in the organic solvent to form a product comprising TFPX-dichloride.
17. The method of claim 16 wherein the reaction is carried out in the presence of a catalyst.
18. The method of claim 17 wherein the catalyst is selected from the group consisting of $SbCl_3$, $SbCl_5$, $SbF_3$, $SbF_5$, $HgF_2$ and $SnCl_4$.

19. A synthesis method comprising the steps of:
a) providing a first reactant comprising hexachloro-p-xylene;
b) providing a second reactant comprising anhydrous HF;
c) providing an organic solvent, the solvent being substantially immiscible with HF and substantially non-reactive with HF and hexachloro-p-xylene;
d) reacting the first and second reactants in the organic solvent to form a product comprising TFPX-dichloride;
e) reacting the TFPX-dichloride product to form a parylene dimer; and
f) reacting the parylene dimer using the Gorham process to form polymeric parylene.

20. The method of claim 19 wherein the organic solvent is selected from the group consisting of methylene chloride, 1,1,2,2-tetrachloroethane, pentane, hexane, toluene, 1,2-dichloroethane and mixtures thereof.

21. The method of claim 19 wherein the organic solvent comprises 1,2-dichloroethane.

22. The method of claim 19 wherein the reaction between the first and second reactants is carried out in the presence of a catalyst.

23. The method of claim 22 wherein the catalyst is selected from the group consisting of $SbCl_3$, $SbCl_5$, $SbF_3$, $SbF_5$, $HgF_2$ and $SnCl_4$.

* * * * *